United States Patent [19]

Harris et al.

[11] 4,152,415

[45] May 1, 1979

[54] METHOD OF INCREASING THE EFFECTIVENESS OF ORAL VACCINATION FOR SWINE DYSENTERY

[75] Inventors: Delbert L. Harris, Ames, Iowa; Robert A. Goodnow, Omaha, Nebr.

[73] Assignees: Iowa State University Research Foundation, Inc., Ames, Iowa; Chromalloy American Corporation, Clayton, Mo.

[21] Appl. No.: 935,062

[22] Filed: Aug. 18, 1978

[51] Int. Cl.² .................. A61K 39/02; A61K 9/28; A61K 9/30; A61K 9/36
[52] U.S. Cl. .................................... 424/16; 424/35; 424/92
[58] Field of Search ............... 424/16, 31, 35, 88, 424/89, 92, 93

[56] References Cited

U.S. PATENT DOCUMENTS

| | | | |
|---|---|---|---|
| 2,369,218 | 2/1945 | Dick et al. | 424/92 X |
| 2,946,724 | 7/1960 | Valentine | 424/89 |
| 3,072,528 | 1/1963 | Kludas et al. | 424/93 |
| 3,081,233 | 3/1963 | Enz et al. | 424/35 X |
| 3,127,318 | 3/1964 | Eversole et al. | 424/92 X |
| 3,317,393 | 5/1967 | Chanock et al. | 424/89 X |
| 3,458,621 | 7/1969 | Tint | 424/35 X |
| 3,541,203 | 11/1970 | Fogle et al. | 424/93 X |
| 3,823,228 | 7/1974 | Ferris et al. | 424/35 |

OTHER PUBLICATIONS

Hudson M. J. et al., Res. Vet. Sci. 1976 21(3): 366–367, Swine Dysentery Protection of Pigs by Oral and Parenteral Immunization with Attenuated Treponema Hyodysenteriae.

*Primary Examiner*—Shep K. Rose
*Attorney, Agent, or Firm*—Timothy L. Tilton; Herbert B. Roberts

[57] ABSTRACT

The resistance of field-raised swine to dysentery infection is increased by a sequence of parenteral and oral administrations. First there is parenterally administered to the swine an injectable cell concentrate containing a virulent isolate of killed cells of *Treponema hyodysenteriae,* and not less than five days after the animals have received the first of the parenteral injections, a series of oral administrations of enteric-coated pellets is started, the pellets containing concentrated killed cells of a virulent isolate of *T. hyodysenteriae.* The oral administrations are given at least once every 24 hours for a period of at least five days.

10 Claims, No Drawings

METHOD OF INCREASING THE EFFECTIVENESS OF ORAL VACCINATION FOR SWINE DYSENTERY

BACKGROUND AND PRIOR ART

An anaerobic spriochete, *Treponema hyodysenteriae*, has been characterized as the primary etiological agent in swine dysentery. Harris, D. L.; Glock, R. D.; Christensen, C. R.; and Kinyon, J. M.: *Vet. Med./Small Animal Clin.* 67:61 (1972); Taylor, D. J.; and Alexander, T. J. L.: *Brit. Vet. J.* 127:108 (1971). But relatively little is known about the immunology of swine dysentery although resistance to reinfection can be demonstrated in convalescent pigs. In 1976, Glock et al reported that parenteral vaccination of pigs with killed cells of a virulent isolate of *T. hyodysenteriae* provided a significant degree of protection against subsequent intragastric challenge with live virulent *T. hyodysenteriae*. Glock, R. D., Schwartz, K. J., and Harris, D. L., *Proceedings, International Pig Veterinary Society Congress*, June 1976, Ames, Iowa. The vaccine was given in six intravenous injections at 6-day intervals. This was the first reported success in immunizing swine against swine dysentery infection.

Hudson et al found that oral dosing of an attenuated strain of *T. hyodysenteriae* provided no protection against subsequent challenge. Hudson, M. J., Alexander, T. J. L., Lysons, R. J., Wellstead, P. D., *Brit. Vet. J.* (1974) 130:37. Subsequently, Hudson et al attempted to immunize pigs with live attenuated *T. hyodysenteriae* using a combination of oral dosing and parenteral inoculation. Hudson, M. J., Alexander, T. J. L., Lysons, R. J., Prescott, J. F., *Res. Vet. Science* (1976) 21:366. Oral doses were administered on three consecutive days, and after an interval of several days, intraperitoneal vaccinations were administered, which were followed after several more days with intramuscular vaccinations. The overall results of these tests were summarized as follows: "Although vaccination appeared to enhance immunity to swine dysentery, half of the vaccinated pigs developed the disease. This level of protection would be unlikely to be of practical value in the field."

SUMMARY OF INVENTION

As disclosed in the co-pending application of Robert A. Goodnow, filed on even date herewith, and entitled "Oral Vaccine for Swine Dysentery and Method of Use", the effectiveness of oral vaccines for swine dysentery infection can be improved by administering the vaccine in the form of enteric-coated pellets. This invention is based in part on the discovery that the effectiveness of oral vaccination can be still further improved by first administering a parenteral vaccine. The parenteral vaccine should also contain killed cells of a virulent isolate of *Treponema hyodysenteriae*. The parenteral vaccine appears to act synergistically with the delayed oral vaccine. Although the theoretical explanation for this action has not been definitely established, it appears to involve a kind of antigenic sensitization. Such a phenomenon has been observed by Pierce et al with respect to cholera toxoid in rats. Pierce, N. F. and Gowens, J. L., "Cellular Kinetics of the Intestinal Immune Response to Cholera Toxoid in Rats", *J. Exp. Med.* (1975) 142:1550.

To achieve the benefits of the present invention, it is believed desirable to wait at least five days after the parenteral vaccination before beginning a series of oral administration of enteric-coated pellets. For further sensitization of the animals, a second parenteral dose of the *T. hyodysenteriae* antigen may be given prior to or concurrently with the start of the oral series. In one embodiment, baby pigs are given one or two parenteral vaccinations prior to weaning, and the administration of the oral vaccine is started as soon as the pigs are receiving dry feed, which may be prior to weaning. The oral administration should be continued for several days, such as for at least five days, the oral vaccine being administered once every 24 hours in an orally effective amount.

The oral vaccinations can be conveniently carried out, since the enteric-coated pellets may be in the form of small granules which can be mixed with ground pig feed. Further, parenteral injections may be in intramuscular or subcutaneous form, and not more than 1 to 3 of such injections is needed. Also, the parenteral injections can be given while the pigs are young and lightweight, and therefore easier to handle.

Other features and advantages of the invention will be described in the following specification.

DETAILED DESCRIPTION

The method of the present invention for increasing the resistance of field-raised swine to dysentery infection, comprises a sequence of parenteral and oral administrations which are carried out before the swine have contracted the infection. There is first parenterally administered to the swine an injectable cell concentrate containing a virulent isolate of killed cells of *Treponema hyodysenteriae*. At least one injection is given per animal and each injection should contain at least 2 milligrams (dry basis) of the antigenic cells. The parenteral injection may be repeated, such as a total of 2 to 3 partenteral injections, but it does not appear that more than 2 injections are needed. In one embodiment, the first parenteral injection is given, and after an interval of at least 4 days, a second parenteral injection is administered. The second injection may be prior to or concurrently with the starting of the administration of the oral vaccine. For example, weaned pigs may be given a parenteral injection, and after a delay of 5 to 8 days, a second parenteral injection is given concurrently with the starting of the oral vaccination series. In a variation of this procedure, baby pigs prior to weaning are given at least one parenteral vaccination, and are given the second parenteral vaccination shortly before weaning, and either before or after weaning, the oral vaccination series is started. Such variations come within the scope of the present invention, the essential feature of the method of the present invention being that the parenteral vaccination precedes by several days the oral series. The desirability of this sequence was not recognized by prior art workers, testing oral vaccination for swine dysentery. Hudson et al administered the oral doses first, and after delay of several days, the parenteral vaccinations were administered. See Hudson et al *Res. Vet. Science* (1976) 21:366.

In accordance with the present invention, not less than 5 days after the animals have received the first of the parenteral injections, a series of oral administrations is begun of enteric-coated pellets containing killed cells of a virulent isolate of *Treponema hyodysenteriae*. These oral administrations are preferably given once every 24 hours for a period of at least 5 days. Each oral dose should comprise at least 3 milligrams (dry basis) of the *T. hyodysenteriae*. In one preferred procedure, the oral administrations provide at least 4 milligrams (dry basis) of the antigenic cells per animal, and are continued for at least 8 days at the rate of one oral administration per animal per 24 hours. While the method of this invention can be applied to adult swine, such as breeding sows, it has particular importance for use with growing pigs. As a matter of convenience, the oral administrations are preferably not started until the pigs are receiving dry feed, which may be prior to weaning. The method is particularly applicable to young growing pigs which are referred to as feeder pigs. The parenteral vaccinations, which can be conveniently carried out by intramuscular or subcutaneous injection, can be given before the pigs are weaned, or both before and after weaning.

The present invention can be practiced with any virulent isolate of *T. hyodysenteriae*. Attenuated or non-virulent isolates or strains are not desirable. A virulent isolate or strain is one which is capable of producing a typical swine dysentery infection. One suitable isolate has heretofore been identified in the literature as B204. See Kinyon, J. M., and Harris, D. L.: *Vet. Rec.* (1974): 95:219. Referred to in the same publication is the isolate identified as B234, which can also be used in practicing the present invention. However, type strain B78 (ATCC No. 27164) is not suitable, being non-virulent. Isolates B204 and B234 have been deposited with the American Type Culture Collection; B204 being identified as ATCC No. 31212 and B234 as ATCC No. 31287. It should be understood that these isolates are representative of class of virulent isolates or strains which can be employed.

The *T. hyodysenteriae* cells for preparation of the vaccines can be cultured using trypticase soy broth (TSB) with 10% (v/v) fetal calf serum (FCS). For example, the inoculated broth can be incubated at 37°–38° C. under an anaerobic atmosphere, such as 50:50 $H_2:CO_2$ or $CO_2$ alone. The gaseous atmosphere should be deoxygenated. For further details, see Kinyon, J. M., and Harris, D. L.: *Vet. Rec.* (1974): 95:219.

After the fermentation has been completed, the cells can be recovered and concentrated by centrifugation or ultrafiltration to obtain a cell slurry for further processing. The cells are killed by a suitable procedure, either in the fermenter or after recovery. Standard killing agents may be used such as formalin or merthiolate. For example, a killing-concentration of formalin, such as 0.2% formalin (v/v), can be added to the fermenter or to the concentrated cell slurry. The killed cells of *T. hyodysenteriae, B. vulgatus,* and *F. necrophorum* are used to prepare the vaccines, the cells being concentrated and intermixed in the required proportions.

Where the parenteral preparation is intended for intramuscular injection, it is not believed to be beneficial to use an adjuvant. However, for subcutaneous injection an adjuvant may have some value. For this purpose a meat-animal acceptable adjuvant, such as aluminum hydroxide, can be added. For example, it can be used as a 2 to 5% aqueous solution of aluminum hydroxide (aluminum oxide basis).

The oral preparation should be enteric-coated. As used herein the term "enteric-coated" refers to a coating which is resistant to dissolving in the swine stomach while dissolving in the swine intestines. As disclosed in the co-pending application of Robert A. Goodnow, filed on even date herewith, entitled "Oral Vaccine for Swine Dysentery and Method of Use", such enteric coatings are preferably selected so that they are substantially insoluble in water at a pH below 5.0 while being slowly soluble in water at a pH of 5.8 to 6.2.

Any of the known enteric coatings which meet these solubility or pH conditions can be utilized. One coating material is cellulose acetate phthalate, which may be plasticized with diethyl or dibutyl phthalate so that the coating is more resistant to cracking. For application, the enteric coating material may be dissolved in a suitable volatile organic solvent, and the enteric coat may be built up in a series of applications to assure that the coating will be complete and relatively uniform. One well known procedure of this kind is referred to as the Open-Pan Ladle Coating Process. For example, 30 to 40 parts by weight of cellulose acetate phthalate together with 8 to 10 parts of diethyl phthalate may be dissolved in 250 to 300 parts by weight of acetone to form a coating solution for such application. Suitable resins may also be used, such as acrylic resins prepared for use as enteric coatings. One such product is sold under the trademark "Eudragit L" by Röhm Pharma Gmbh, Darmstadt, West Germany. The release pH of Eudragit L can be increased where desired by mixing it with Eudragit S. The manufacturer (Röhm) describes Eudragit L as soluble in intestinal juice from pH 6.0 and Eudragit S as soluble from pH 7.0. For administration of the enteric-coated vaccines with a feed material, it is preferred to employ from 5 to 20 parts by weight of Eudragit S with from 95 to 80 parts of Eudragit L.

The Wurster Coating Process can also be used to apply the enteric coatings. This process is described in U.S. Pat. Nos. 3,241,520 and 3,253,944. It is carried out as a commercially available service by Coating Place, Inc., Verona, Wis.

The enteric-coated oral vaccine is preferably in the form of pellets or granules which can be readily mixed with swine feed material for administration to the animals. For example, such granules may range from about −20 mesh to +100 mesh (U.S. Standard Screen). The granules are mixed with a finely-divided feed material such as a ground feed used for pigs after weaning. Any swine or pig feed material can be used, such as a basal ration containing ground corn, rolled oats, soybean meal, minerals and vitamins. The coated granules may also be premixed with vitamin-mineral fortification premixes, which are later combined with the other feed ingredients.

To act as a filler or bulk stabilizer for dessication and pellet preparation, standard filler substances may be added to the cell slurry such as sucrose, dextrose, lactose, etc. In general, the amount of filler-stabilizer to be added may range from about 10 to 50 parts by weight of filler per 100 parts of cells (dry basis). Prior to the addition of the filler, the cell concentrate preferably contains in excess of 3.0 milligrams of cells (dry basis) per milliliter of slurry. For example, the cell concentrates may contain from about 4 to 7 milligrams of cells (dry basis) per milliliter of cell slurry. The particular concentration is not critical, since most of the residual water of the slurry is removed by a suitable drying procedure in preparing the pellets.

The mixed cell slurry containing the added binder may be dried by a suitable biological drying procedure such as freeze-drying. Preferably, the drying is carried out at a relatively low temperature, such as below 40° C. The dried material is then pulverized to a finely-divided condition for preparing tablets or granules.

For example, the mixed cell concentrates in the form of liquid slurries are mixed with sucrose and cellulose, and kneaded to a doughy consistency. The dough is then extruded in the form of noodles or ribbons, which are broken up and formed into granules. The granule size is not critical, but desirably is of a size smaller than 20 mesh (U.S. Standard Screen). The granules are dried in an oven at a relatively low temperature such as 37°–40° C. until most of the moisture has been removed. The final moisture content is not critical, and desirably may range from about 1 to 3% by weight.

In applying tablet and granule coatings, a dye may be included as a colorant for the coating. This permits the coating to be more readily inspected for thickness and uniformity, and makes it easier to detect imperfections in the coatings. In practicing the present invention, it is desirable to use a dye in the enteric coatings of the present invention, although it is not essential with respect to the desired immunizing action. Suitable dyes include Lake Blue No. 2 and crystalline violet dye.

While the vaccines of the present invention may be applied to adult swine, such as breeding sows, an important use is with growing pigs. For example, the method may be applied to feeder pigs, starting at the age of about 3 to 8 weeks. The method may also be applied to older pigs during their growth period prior to marketing. The pigs raised under field conditions are highly subject to swine dysentery infection with consequent economic loss due to lowering of the rate of weight gain and the feed efficiency. By increasing the resistance of the pigs to swine dysentery infection, optimum rates of weight gain may be maintained.

In practicing the present invention, the dose level can be related to the amount of $T.\ hyodysenteriae$ administered. For example, with the oral preparations, it is desirable to administer at least 3 milligrams of the killed cells of $T.\ hyodysenteriae$ (dry basis) per animal. Preferably, the doses are administered daily (once every 24 hours), such as by admixture of the enteric-coated granules with a feed material, and the dosing is continued for a period of at least five days, such as from 5 to 15 days. In a preferred embodiment, the oral doses contain at least 4 mg. of the $T.\ hyodysenteriae$ cells (dry basis) per dose, such as doses in the range of 4 to 6 mg.

For the parenteral vaccine, it is preferred to inject at least 2 milligrams (dry basis) of $T.\ hyodysenteriae$ cells per animal per dose. If necessary, the parenteral dose can be repeated, such as a total of from 2 to 3 doses. In a preferred embodiment, the parenteral dose may contain from 3 to 6 mg. (dry basis) of $T.\ hyodysenteriae$ cells per dose.

The method of this invention can also be practiced by using the combination vaccine for swine dysentery described in the co-pending application of Delbert L. Harris, Robert A. Goodnow, Robert D. Glock, and Joann M. Kinyon, filed on even date herewith, and entitled "Combination Vaccine for Swine Dysentery and Method of Use". More specifically, the oral vaccine may contain other bacteria in addition to $T.\ hyodysenteriae$, such as *Bacteroides vulgatus*, or *Fusobacterium necrophorum*, or mixtures thereof. For example, at least one of these other bacteria may be present in an amount of from 0.25 to 2 parts by weight (dry basis) per part of $T.\ hyodysenteriae$ cells, the additional bacteria being present in the form of concentrated killed cells. The parenteral preparation may also contain concentrated killed cells of *B. vulgatus* in the amount of from 0.25 to 2 parts by weight (dry basis) of the *B. vulgatus* cells per part of the $T.\ hyodysenteriae$ cells.

The invention is further illustrated by the following examples.

EXAMPLE I

Organism

The microorganism, *Treponema hyodysenteriae*, Strain 204 (ATCC No. 31287) was grown in Trypticase Soy Broth containing 5–10% sterile Fetal Calf Serum (GIBCO Laboratories, Grand Island, N.Y.) in test tubes, 500 cc Erlenmeyer flask, 4-liter glass jugs and in a 25-liter pilot New Brunswick fermentor. The growth culture was maintained until log phase growth ceased. 50:50 $H_2:Co_2$ or no gas was used to maintain the gaseous atmosphere in the fermentor during the growth period. After the fermentation had been completed, the cells were concentrated in liquid mass by ultrafiltration.

The cell culture was forced by positive air pressure through a 100,000 molecular weight size membrane. The cell slurry was concentrated to a final concentration of 4.0 milligrams dry weight measurement per ml of culture. Ten percent (10%) by volume sterile milk stabilizer, (50% Carnation Milk Powder in 50% $H_2O$) was added to the antigen $T.\ hyodysenteriae$ slurry. E.g. 750 ml culture at 4 milligrams antigen/ml or 3.0 gram of antigen added to 75 ml milk stabilizer containing 37.5 grams dry powdered milk and 37.5 ml $H_2O$. The antigen-milk stabilizer mixture was freeze-dried in a commercial freeze drier for 18 hours. The temperature was never allowed above 37° C. during the drying of the mixture. 66.20 Grams of dried material was recovered from the drying process.

Capsule Preparation

Ten percent (10%) by weight dry soluble starch was added to the dried material giving the following components:

3.0 grams active antigen $T.\ hyodysenteriae$ (killed cells-dry basis)

0.3 grams powdered milk stabilizer 0.33 grams soluble starch binder 0.5 Gram mixture (3 mg dry basis active $T.\ hyodysenteriae$ antigen) of the above mixture was placed in a hand-operated pellet press. A ⅜" punch and die set was used to give a tablet of approximately ⅜" thickness by ½" in diameter.

Each tablet was coated with an enteric coating which upon contact in a chemical environment pH 6 or greater, will degrade and release the antigenic material into the colonic lumen. The coating is not soluble at the stomach pH.

Enteric Delivery System

1. Enteric Coating Solution *(36.0 grams of cellulose acetate phthalate, 9.0 grams of diethyl phthalate, and 0.2 grams of crystalline violet dye) was diluted into 255 grams of reagent grade acetone. (For a description of a similar procedure, see C. J. Malm, J. Amer. Phar. Assoc. Science Edition, Vol. 40, p. 520, 1951.)

2. Enteric Coat Application—Each tablet was air blasted to remove dust and was submerged under the surface of the coating solution at least twenty times, with complete air drying of tablets between coatings.

3. Wax Coating—The enteric coating was further protected from $H_2O$ uptake by application of a white wax ("Be Square" 195, Petrolite Corporation, Bareco Division, Tulsa, Okla.). This was liquefied in the GI tract, and in no way inhibits the antigen release in the colon. Ten (10) grams of "Be Square" 195 wax beads were dissolved in 10 ml of acetone. Each enteric coated tablet was submerged at least twice in the liquid wax solution. The wax coat was allowed to dry prior to tablet bulking and storage.

Parenteral Vaccines:

The test also included administration of parenteral vaccine prepared as follows: The concentrated liquid slurry described above (4.0 mg. *T. hyodysenteriae* cells dry basis per ml) was diluted from 4.0 mg/ml to 1.0 mg/ml with a 20% solution of sterile aluminum hydroxide adjuvant. The resulting parenteral vaccine contained about $2.5 \times 10^9$ killed cells per milliliter.

Materials and Methods

Experimental Animals—Sixteen (16) pigs from a herd with no history of swine dysentery were placed in swine testing facilities at approximately five weeks of age and fed a 16% protein grown ration containing no drugs.

Preparation of Vaccines—An orally delivered enteric release vaccine and a parenteral vaccine containing *Treponema hyodysenteriae* Isolate B204 (ATCC No. 31287) with aluminum hydroxide as adjuvant were prepared as described above.

Preparation of Inoculum—Cultures of *Treponema hyodysenteriae* (Isolate B204) were grown approximately 24 hours in aerobically prepared trypticase soy broth containing 10% fetal calf serum under deoxygenated $H_2:CO_2$ at 37° C. Seventy-five (75) ml of whole culture containing approximately $5 \times 10^8$ organisms per ml was administered to each pig via stomach tube following a 48 hour starvation period. The isolate of *T. hyodysenteriae* had not been passaged more than eight (8) times in vitro.

Experimental Design—The sixteen (16) pigs were randomly assigned to individual pens. The pigs were immunized as follows:

| GROUP | NO. OF PIGS | PARENTERAL VACCINE SUBCU- TANEOUS* | INTRAPER- ITONEAL* | ORAL VACCINE* |
|---|---|---|---|---|
| I | 4 | | + | + |
| II | 4 | + | − | + |
| III | 8 | − | − | − |

*+ = administered;
− = not administered

On Day 0, the pigs in Group I were injected with 5 ml/pig of the parenteral vaccine. Pigs in Group II were injected with a similar amount/pig by subcutaneous route. On Day 14, a 5 ml/pig booster vaccination was given by respective routes. On Day 19, each pig in Groups I and II were given one (1) oral tablet per day through the 29th day. On day 30, all pigs were weighed. Feed was withheld on days 30 and 31. On day 32, rectal swabs were collected and all pigs were challenged with *T. hyodysenteriae* as described above. Clinical evaluation of response to challenge was recorded for each pig on a twice daily basis for 40 days post inoculation. On day 40 post-inoculation, each pig was weighed.

Evaluation of Response to Challenge—Each pig was observed twice daily and 3 clinical parameters were scored on a scale of 1 to 3. The results are shown in Table A.

TABLE A

| | Group | | |
|---|---|---|---|
| Clinical response | I N=4[a] | II N=4 | III N=8 |
| Diarrhea: | | | |
| Day of Onset[b]/Post Inocul. | 16 | 5.2 | 13.6 |
| Days Duration | 4 | 8.2 | 11.8 |

TABLE A-continued

| | Group | | |
|---|---|---|---|
| Clinical response | I N=4[a] | II N=4 | III N=8 |
| No. Affected | 4 | 4 | 6 |
| Dysentery: | | | |
| Day of Onset/Post Inocul. | 25.7 | 24.2 | 17.6 |
| Days Duration | 3.2 | 2.5 | 5 |
| No. Affected | 2 | 2 | 5 |

[a]N equals number of pigs per group
[b]Study terminated at 40 days. Calculations are based on a value of 40 assigned to each pig which remained normal.

General Condition:
1 = Normal
2 = Gaunt, mildly inactive
3 = Emaciated, moribund Feces Consistency:
1 = Normal, firm
2 = Soft, not formed
3 = Liquid Feces Composition:
1 = Normal
2 = Increased mucus
3 = Large amount of blood present Observation of *T. hyodysenteriae* Like Organisms—Rectal swabs were collected. A drop of each sample was reviewed under a dark field microscope observation. There was a significant increase in the numbers of *T. hyodysenteriae* like organisms in clinically affected pigs, which was considered evidence of an ongoing swine dysenteriae infection.

Weight Gain—The average weight gain during the period from day of challenge inoculation to the day of study termination was compared between vaccinated and non-vaccinated groups. The results are shown in Table B.

TABLE B

| | Group | | |
|---|---|---|---|
| | I | II | III |
| Days Post Test Initiation | IP-Oral | SC-Oral | Controls |
| 0 | 26.0 | 27.6 | 31.1 |
| 40 | 103.0 | 110.2 | 94.0 |
| Total Average Gain per pig | 77.0 | 82.6 | 62.9 |

EXAMPLE II

Materials and Methods

Experimental Animals—Pigs from a herd with no history of swine dysentery were placed in isolation units at approximately 8 weeks of age and fed a 16% protein grower ration which contained no drugs.

Preparation of Inoculum—Cultures of *Treponema hyodysenteriae* (isolate B204) were grown approximately 24 hours in aerobically prepared trypticase soy broth containing 10% fetal calf serum under deoxygenated $H_2:CO_2$ at 38° C. One hundred ml of whole culture was administered to each pig via stomach tube following a 48 hour starvation period. The isolate of *T. hyodysenteriae* had not been passaged more than 15 times in vitro.

Preparation of Vaccines—An oral vaccine and a parenteral vaccine were prepared containing *Treponema hyodysenteriae* isolate (B204, No. 31212) and *Bacteroides vulgatus* (Strain 28, ATCC No. 31376).

A. Preparation of *Treponema hyodysenteriae* Antigen

Growth

The *T. hyodysenteriae* organism was grown in trypticase soy broth enriched with 10% fetal calf serum (Gibco, Grand Island, N.Y.) in a 28-liter pilot New Brunswick fermenter and grown to an average cell mass level of equal to or greater than $2.0 \times 10^9$ cells/ml. Seventy-two (72) liters of *T. hyodysenteriae* grown to 1.25 milligrams dry wt. antigen/ml of fermenter culture was used in this preparation.

Concentration

The cell culture was inactivated with a 1:10,000 concentration Merthiolate. The cell mass was concentrated by forcing the cell mass through a 100,000 molecular weight size membrane by positive air pressure. The cell slurry was concentrated to a level of 30 milligrams dry wt. antigen/ml per 3.5 liters of slurry.

B. Preparation of *Bacteroides vulgatus* Antigen

The *B. vulgatus* organism was grown in standard peptone yeast extract glucose media to a level of 2.3 milligrams dry wt. antigen/ml fermenter grown culture. Forty-five (45) liters of this cell culture was concentrated by similar ultrafiltration to a cell mass level of 34.7 milligrams dry wt. antigen/ml per 3 liters slurry.

C. Preparation of Combination Antigens

The 3.5 liters of *T. hyodysenteriae* slurry and 3.0 liters of *B. vulgatus* were combined in a common vessel. This slurry was concentrated by similar ultrafiltration to 2.85 liters of slurry.

D. Preparation of Enteric Coat on Vaccine

Carrier:

Twenty (20) mesh sucrose pariels were sprayed with the bacterial antigen slurry to a 15.97% antigen/product wt. increase. Drying temperatures were maintained between 102°–110° F. above the drying bed and between 144°–165° F. on the inlet slurry line. After the antigen was coated upon the sugar seeds, an enteric resin overcoat was sprayed on the antigen-sugar seeds.

E. Enteric Solution 83.3 Grams Eudragit L90, and 25 grams of diethyl phthalate was added to 1.0 liters of methanol. This solution was then q.s. to 1.67 liters with acetone. This solution was sprayed on the sugar-antigen carrier and air dried according to the Wurster Process. See U.S. Pat. Nos. 3,253,944 and 3,241,520. The Wurster coating process was performed by Coating Place, Inc., Verona, Wis. One (1) liter of concentrated slurry resulted in 1 kilogram of oral swine dysentery vaccine.

Experiment 1

Thirty-four pigs were randomly assigned to individual isolation units. The pigs were immunized as follows:

| Group | No. of Pigs | Parenteral Vaccine Intramuscular | Parenteral Vaccine Intraperitoneal | Oral Vaccine |
|---|---|---|---|---|
| I | 9 | + | − | − |
| II | 9 | + | − | + |
| III | 8 | − | + | + |
| IV | 8 | − | − | − |

On day 0 the pigs were weighed individually and pigs in groups I, II, and III were injected with 5 ml/pig of the parenteral vaccine. Starting on day 9, the oral vaccine was fed to the pigs in groups II and III by mixing 1.0 gram of the vaccine in approximately 500 grams of feed which was spred across the floor for consumption by the pigs. Additional feed containing no vaccine was given later. The oral vaccine was administered daily through day 23. On day 14, the pigs in groups I, II, and III were injected with 5 ml/pig of the parenteral vaccine. On day 24, all pigs were weighed. Feed with withheld on days 24 and 25. On day 26, rectal swabs were collected and all pigs were challenged with *T. hyodysenteriae* ($8.0\times10^9$ organisms per pig).

Experiment 2

Forty-five pigs were randomly assigned to isolation units. The pigs were immunized as follows:

| Group | No. of Pigs | Parenteral Vaccine Intramuscular | Oral Vaccine |
|---|---|---|---|
| I | 8 | + | − |
| II | 9 | − | +* |
| III | 9 | + | +* |
| IV | 10 | + | +* (continuous) |
| V | 9 | C** | C** |

*Group II and III received oral vaccine daily until challenge; Group IV received oral vaccine daily before and after challenge.
**Received control placebo-no *T. hyodysenteriae* or *B. vulgatus* antigen.

On day 0 the pigs were weighed individually and pigs in groups I, III, and IV were injected with 5 ml/pig of parenteral vaccine. On day 8 the oral vaccine was initiated in groups II, III, and IV as described above. The oral vaccine was continued through day 28 for groups II and III. On day 15 the pigs in groups I, III, and IV were injected with 5 ml/pig of parenteral vaccine. On day 28 all pigs were weighed. Feed was withheld on days 29 and 30. On day 31, rectal swabs were collected and all pigs were challenged with *T. hyodysenteriae* ($9.0\times10^9$ organisms per pig).

Pigs were weighed at weekly intervals after challenge and rectal swabs were collected twice weekly. Clinical evaluation of response to challenge was recorded for each pig on a daily basis for 34 days post-inoculation (DPI).

Evaluation of Response to Challenge—Each pig was observed daily and 3 clinical parameters were scored on a scale of 1 to 4.

General Condition:
1=normal;
2=gaunt, mildly inactive;
3=very gaunt, rough hair, very inactive;
4=emaciated, moribund.

Feces Consistency:
1=normal, firm;
2=soft, not formed;
3=liquid;
4=watery.

Feces Composition:
1=normal;
2=increased mucus;
3=increased mucus, small flecks of blood;
4=large amount of blood present.

For purposes of tabulation, a score of 3 or 4 was considered to be respectively cachexia, diarrhea and dysentery in the 3 parameters observed.

A daily index for each pig was calculated as the mean of the scores for the 3 individual observations. Pigs that died were given the maximum score of 4 for each of the parameters through the remainder of the study for purposes of analysis.

Isolation of *T. hyodysenteriae*—A rectal swab was collected and placed in a culturette holder containing transport medium. The swab was held at 4° C. and inoculated onto selective medium for isolation of *T. hyodysenteriae* within 24 hours of collection. The selective medium contained trypticase soy agar, 5% bovine blood, and 400 mcg/ml of Spectinomycin sulfate and was incubated under 80% $H_2$ and 20% $CO_2$ with palladium catalysts at 42° C. The selective medium was examined at 2, 4, and 6 days of incubation and the presence or absence of pathogenic (hemolytic) *T. hyodysenteriae* was recorded.

Necropsy Procedures—A necropsy was performed on all pigs that died during the trial. Macroscopic lesions were recorded and a swab was collected from the colonic mucosa for isolation of *T. hyodysenteriae*. Salmonella isolations were attempted from the mesenteric lymph node, small intestine and colon.

The data is set out below in Tables A, B, and C for Experiment 1 and Tables D, E, and F for Experiment 2.

Results and Discussion

Exp. 1—Some pigs in all vaccinated groups (I, II, and III) showed symptoms of diarrhea and dysentery but of much less severity and duration than nonvaccinated control pigs (group IV). The incubation period of the disease was delayed in vaccinated pigs are compared to nonvaccinated pigs. Vaccinated pigs gained weight more rapidly and gained more total weight than nonvaccinated pigs.

*Treponema hyodysenteriae* were isolated from the feces of pigs in the nonvaccinated groups with 4 days post inoculation. By contrast, most vaccinated pigs did not shed *T. hyodysenteriae* until 14 days post inoculation. Vaccination did not stop the establishment of infection by *T. hyodysenteriae*.

One pig died in the nonvaccinated group due to swine dysentery. No pigs died in the vaccinated groups.

Exp. 2—The pigs in this study appeared to be more severely challenged than Exp. 1. Pigs in group III had less clinical signs of swine dysentery and performed better based on weight gains than pigs in group V (controls). Pigs in group IV were severely affected very early after challenge which may have been due to the continual exposure to the oral vaccine. By contrast, this was the only group in which no deaths occurred.

Seven pigs died during the study. Six of these pigs died of swine dysentery while one pig in group II died of necroproliferative enteritis.

TABLE A

Clinical Responses in Pigs Inoculated Intragastrically with *T. hyodysenteriae* Exp. 1

| | Group | | | |
|---|---|---|---|---|
| Clinical response | I N=9[a] | II N=9 | III N=8 | IV N=8 |
| Diarrhea: | | | | |
| Day of Onset[b] | 15.33 | 25.00 | 21.63 | 12.25 |
| Days Duration | 6.67 | 2.78 | 2.88 | 15.13 |
| No. Affected | 6 | 6 | 5 | 8 |
| Dysentery: | | | | |
| Day of Onset | 21.33 | 25.22 | 24.00 | 14.00 |
| Days Duration | 4.89 | 1.11 | 1.13 | 9.63 |
| No. Affected | 5 | 5 | 4 | 7 |
| Cachexia: | | | | |
| Day of Onset | 29.00 | 34.00 | 34.00 | 18.63 |
| Days Duration | 1.78 | 0 | 0 | 5.50 |
| No. Deaths | 0 | 0 | 0 | 1 |

TABLE A-continued

Clinical Responses in Pigs Inoculated Intragastrically with *T. hyodysenteriae* Exp. 1

| | Group | | | |
|---|---|---|---|---|
| Clinical response | I N=9[a] | II N=9 | III N=8 | IV N=8 |
| Combined Index | 1.46 | 1.25 | 1.27 | 1.97 |

[a]N equals number of pigs per group
[b]Study terminated at 34 days. Calculations are based on a value of 34 assigned to each pig which remained normal.

TABLE B

Cumulative Average Gain (pounds) per Pig Inoculated Intragastrically with *T. hyodysenteriae* Exp. 1

| Days Post inoculation | Group | | | |
|---|---|---|---|---|
| | I | II | III | IV |
| 7 | 6.66 | 6.00 | 5.75 | 3.00 |
| 14 | 11.33 | 15.00 | 12.25 | .25 |
| 21 | 20.11 | 23.11 | 20.25 | 9.36 |
| 28 | 29.33 | 28.45 | 26.12 | 18.07 |
| 35 | 40.00 | 39.56 | 35.75 | 25.07 |

TABLE C

Isolation of Pathogenic *T. hyodysenteriae* from the Feces of Pigs Inoculated Intragastrically with *T. hyodysenteriae* Exp. 1

| Days Post inoculation | Group | | | |
|---|---|---|---|---|
| | I | II | III | IV |
| 0 | 0/9[a] | 0/8 | 0/8 | 0/7 |
| 4 | 0/9 | 0/9 | 0/8 | 2/8 |
| 7 | 4/9 | 1/9 | 2/8 | 4/8 |
| 11 | 7/9 | 8/9 | 3/8 | 8/8 |
| 14 | 8/9 | 8/9 | 6/8 | 7/7 |
| 21 | 619 | 5/7 | 5/8 | 6/7 |
| 28 | 7/8 | 5/9 | 5/8 | 5/7 |

[a]Denominator equals number of pigs sampled. Numerator equals number of pigs positive.

TABLE D

Clinical Responses in Pigs Inoculated Intragastrically with *T. hyodysenteriae* Exp. 2

| | Group | | | | |
|---|---|---|---|---|---|
| Clinical Response | I N=8[a] | II N=9 | III N=9 | IV N=10 | V N=9 |
| Diarrhea: | | | | | |
| Day of Onset[b] | 16.00 | 12.33 | 21.33 | 9.0 | 12.78 |
| Days Duration | 9.63 | 4.78 | 3.56 | 8.2 | 10.22 |
| No. Affected | 7 | 8 | 8 | 10 | 9 |
| Dysentery: | | | | | |
| Day of Onset | 16.00 | 13.22 | 21.78 | 8.9 | 13.00 |
| Days Duration | 6.38 | 4.78 | 2.44 | 6.5 | 8.67 |
| No. Affected | 7 | 8 | 8 | 10 | 9 |
| Cachexia: | | | | | |
| Day of Onset | 25.88 | 14.78 | 27.22 | 17.7 | 17.11 |
| Days Duration | 6.13 | 7.44 | 1.44 | 4.1 | 7.22 |
| No. Deaths | 1 | 2 | 2 | 0 | 2 |
| Combined Index | 1.78 | 1.64 | 1.39 | 1.64 | 1.91 |

[a]N equals number of pigs per group
[b]Study terminated at 35 days. Calculations are based on a value of 35 assigned to each pig which remained normal.

TABLE E

Cummulative Average Gain (pounds) per Pig Inoculated Intragastrically with *T. hyodysenteriae* Exp. 3

| Days Post inoculation | Group | | | | |
|---|---|---|---|---|---|
| | I | II | III | IV | V |
| 7 | −.12 | −1.00 | 6.22 | 3.10 | 3.56 |
| 14 | 2.25 | 1.53 | 5.89 | −5.60 | 5.28 |
| 21 | 4.68 | 3.03 | 10.00 | .10 | 1.35 |
| 28 | 11.54 | 6.36 | 17.00 | 5.90 | 7.07 |
| 35 | 16.68 | 18.50 | 21.97 | 11.80 | 13.64 |

TABLE F

Isolation of Pathogenic *T. hyodysenteriae* from the Feces of Pigs Inoculated Intragastrically with *T. hyodysenteriae* Exp. 2

| Days Post inoculation | Group | | | | |
|---|---|---|---|---|---|
| | I | II | III | IV | V |
| 0 | 0/8[a] | 0/9 | 0/9 | 0/10 | 0/9 |
| 4 | 2/8 | 1/9 | 1/9 | 3/10 | 0/9 |
| 7 | 6/8 | 4/9 | 0/9 | 9/10 | 5/9 |
| 11 | 2/8 | 6/8 | 5/9 | 9/10 | 7/9 |
| 14 | 4/8 | 5/8 | 3/9 | 8/10 | 6/8 |
| 18 | 3/7 | 6/8 | 2/8 | 6/10 | 6/7 |
| 21 | 2/7 | 6/8 | 4/8 | 5/10 | 4/7 |
| 25 | 3/7 | 3/7 | 3/8 | 1/10 | 2/7 |
| 28 | 2/7 | 4/7 | 4/8 | 0/10 | 4/7 |
| 32 | 0/7 | 0/7 | 0/7 | 0/10 | 0/7 |
| 35 | 0/7 | 2/7 | 0/7 | 0/10 | 0/7 |

[a]Denominator equals number of pigs sampled. Numerator equals number of pigs positive.

EXAMPLE III

*T. hyodysenteriae* and *B. vulgatus* antigenic preparations comprising concentrated killed cells are prepared as described in Example II. Each concentrate is diluted with sterile water to a concentration of 2 mg/ml, and equal volumes of the diluted antigens are then mixed to provide a final combined concentration of 1 mg/ml for each antigen. This preparation is used for intramuscular injection without the addition of an adjuvant.

Enteric-coated orally-administrable granules containing killed cells of both antigens are prepared as described in Example II, except that 15 parts by weight of Eudragit S 90 (90% active, 10% water) are mixed with 85 parts of Eudragit L 90 (90% active, 10% water) to produce a coating having greater resistance to dissolving in the stomach when the pigs are being fed continuously. (Eudragit S 90 and L 90 are sold by Röhm Pharma Gmbh, Darmstadt, West Germany.) These granules are used for oral administration in admixture with dry pig feed, such as a basal ration containing ground corn, rolled oats, soybean meal, minerals and vitamins.

Suckling pigs at seven days of age are each given an intramuscular injection providing 3 mg of each of the *T. hyodysenteriae* and *B. vulgatus* antigens. Fourteen days later when the pigs are 21 days of age, each of the pigs is given a second intramuscular injection providing the same amount of the antigens as the first injection. On the same day, since the pigs had been receiving some dry feed prior to weaning, the administration of the oral vaccine is started. The enteric-coated granules are proportioned in relation to the amount of feed so that each pig receives an average of 5 mg of each anitgen during each 24 hour period. The oral administration is continued for at least 10 days, and preferably longer, such as from 2 to 6 weeks.

We claim:

1. The method of increasing the resistance of field-raised swine to dysentery infection, comprising a sequence of parenteral and oral administrations which are carried out before the swine contract the infection, characterized by:
   (a) first parenterally administering to the swine an injectable cell concentrate containing a virulent isolate of killed cells of *Treponema hyodysenteriae* at least one injection being given per animal and each injection containing at least 2 milligrams (dry basis) of said cells; and
   (b) not less than 5 days after said animals have received the first of said parenteral injections beginning a series of oral administrations of enteric-coated pellets containing concentrated killed cells of a virulent isolate of *Treponema hyodysenteriae*, said oral administrations being given at least one every 24 hours for a period of at least 5 days, and each of said oral administrations providing at least 3 milligrams (dry basis) of said cells.

2. The method of claim 1 in which said killed cells of *Treponema hyodysenteriae* are prepared from isolate B204 (ATCC No. 31287).

3. The method of claim 1 or claim 2 in which said parenteral injections comprise 2 injections per animal with an interval of at least 4 days between the days on which the injections are given, and each parenteral injection provides at least 3 milligrams (dry basis) of said cells of *Treponema hyodysenteriae*.

4. The method of claim 1 or claim 2 in which each of said oral administrations provide at least 4 milligrams (dry basis) of said cells per animal and are continued for at least 8 days at the rate of one oral administration per animal per 24 hours.

5. The method of claim 1 or claim 2 in which said swine are growing pigs, and said oral administrations are started after the pigs have been weaned.

6. The method of increasing the resistance of field-raised swine to dysentery infection, comprising a sequence of parenteral and oral administrations which are carried out before the swine contract the infection, characterized by:
   (a) first parenterally administering to the swine an injectable cell concentrate containing a virulent isolate of killed cells of *Treponema hyodysenteriae*, at least two injections being given per animal with an interval of at least 4 days between the days on which the injections are given, and each injection containing at least 2 milligrams (dry basis) of said cells; and
   (b) not less than 5 days after said animals have received the first of said injections beginning the feeding of enteric-coated granules containing concentrated killed cells of a virulent isolate of *Treponema hyodysenteriae*, said feeding being at the rate of at least 3 milligrams (dry basis) per animal per 24-hour day, and being continued for at least 5 days.

7. The method of claim 6 in which said cell so *Treponema hyodysenteriae* are prepared from isolate B204 (ATCC No. 31287).

8. The method of claim 6 or claim 7 in which said parenteral administration is intramuscular injection.

9. The method of claim 6 or claim 7 in which said swine are baby pigs, and at least the first of said parenteral administrations is given before said pigs are weaned, said feeding of said granules being started after said pigs have been weaned.

10. The method of claim 9 in which said parenteral administration is intramuscular injection.

* * * * *

UNITED STATES PATENT OFFICE
CERTIFICATE OF CORRECTION

Patent No. 4,152,415      Dated May 1, 1979

Inventor(s) Delbert L. Harris and Robert A. Goodnow

It is certified that error appears in the above-identified patent and that said Letters Patent are hereby corrected as shown below:

Column 14, line 51 change "cell so" to --cells of--.

Signed and Sealed this

Twenty-fifth Day of September 1979

[SEAL]

Attest:

LUTRELLE F. PARKER

Attesting Officer     Acting Commissioner of Patents and Trademarks

UNITED STATES PATENT OFFICE
CERTIFICATE OF CORRECTION

Patent No. 4,152,415     Dated May 1, 1979

Inventor(s) Delbert L. Harris and Robert A. Goodnow

It is certified that error appears in the above-identified patent and that said Letters Patent are hereby corrected as shown below:

Col. 6, line 7, change "31287" to --31212--.

Col. 7, line 20, change "31287" to --31212--.

Col. 14, line 15, change "31287" to --31212--.

Col. 14, line 53, change "31287" to --31212--.

Signed and Sealed this

Twenty-seventh Day of November 1979

[SEAL]

Attest:

RUTH C. MASON
Attesting Officer

LUTRELLE F. PARKER
Acting Commissioner of Patents and Trademarks